United States Patent [19]

Imonti

[11] Patent Number: 4,754,750

[45] Date of Patent: Jul. 5, 1988

[54] AREOLA/NIPPLE SURGICAL WOUND PROTECTOR

[75] Inventor: Maurice M. Imonti, Dana Point, Calif.

[73] Assignee: CooperVision, Inc., Palo Alto, Calif.

[21] Appl. No.: 28,673

[22] Filed: Mar. 20, 1987

[51] Int. Cl.⁴ .............. A61F 13/00; A61F 15/00; A61L 15/00
[52] U.S. Cl. .................. 128/155; 128/150; 128/156; 128/132 R; 604/346; 450/39; 450/81
[58] Field of Search .......... 128/150, 155, 156, 132 R, 128/360; 206/222; 215/11 C, 11 R, 11 B; 604/346; 623/7, 8; 450/39, 40, 57, 81

[56] References Cited

U.S. PATENT DOCUMENTS

| 1,967,923 | 7/1934 | Connolly | 128/156 |
| 2,448,938 | 9/1948 | Wayne | 604/346 |
| 2,495,307 | 1/1950 | Abramson | 128/150 |
| 2,604,092 | 7/1952 | Brown et al. | 604/346 X |
| 3,677,225 | 7/1972 | Czirely | 128/132 R |
| 4,333,471 | 6/1982 | Nakai | 128/150 |

FOREIGN PATENT DOCUMENTS

| 0836238 | 4/1952 | Fed. Rep. of Germany | 128/150 |
| 2464064 | 4/1981 | France | 128/156 |
| 2577798 | 8/1986 | France | 128/156 |
| 0007772 | of 1893 | United Kingdom | 128/150 |

Primary Examiner—Richard J. Apley
Assistant Examiner—Paul Prebilic
Attorney, Agent, or Firm—Vorys, Sater, Seymour & Pease

[57] ABSTRACT

An aerola/nipple surgical wound protector including a sterile pad having an upper surface, a lower non-stick surface and a centrally-located pad opening through it and engaging the upper and lower surfaces. A transparent cone-shaped nipple protector member having an outwardly-disposed flange at its base portion is secured via the flange to the upper pad surface over the pad opening. The nipple protector member has an opening in its base portion, a dome with air holes therethrough at its opposite end, and an interior configured to receive the patient's nipple up through the opening and into the protector member. Four spaced adhesive tape strips extend radially out from the pad for securing the pad and protector member over the patient's nipple.

13 Claims, 1 Drawing Sheet

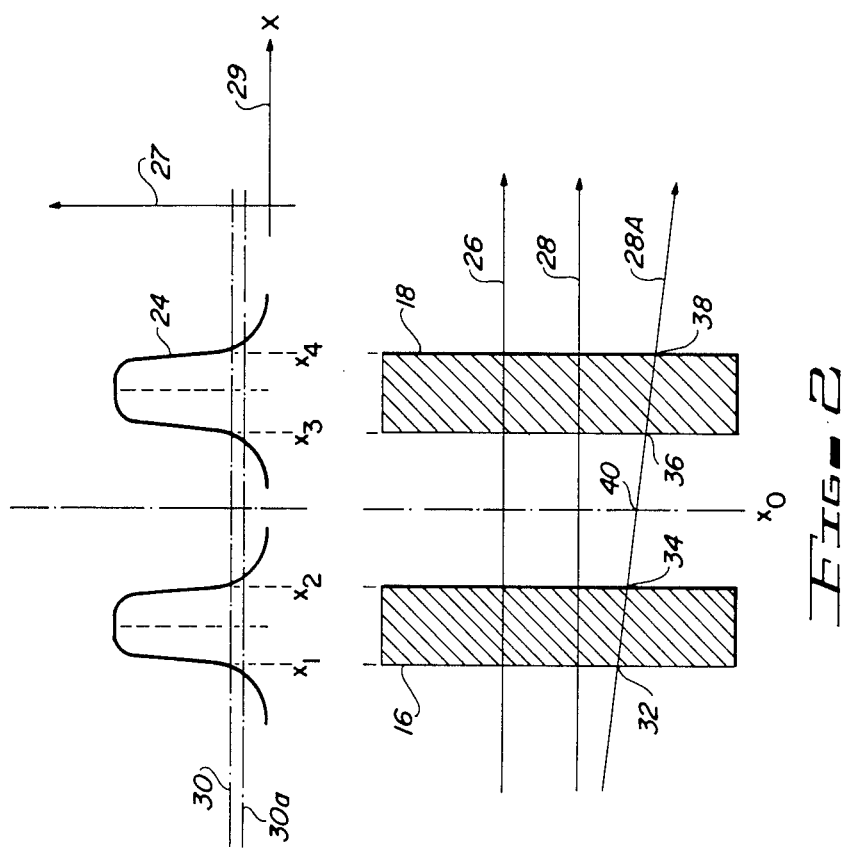
FIG-2A
FIG-2
FIG-1
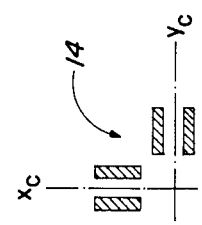

AREOLA/NIPPLE SURGICAL WOUND PROTECTOR

BACKGROUND OF THE INVENTION

The present invention relates to bandages and more particularly to surgical bandages for the areola and nipple area of a woman's breast following a radical mastectomy.

Following a radical mastectomy it is necessary to rebuild the patient's breast. Silicone implants are implanted to give the breast the needed mass. Tissue is taken from the vaginal area or ear lobe to construct the nipple and then the surrounding area is tattooed to match the coloring of the woman's other breast. In the past to then protect the surgically created nipple and surrounding areola several loose sterile pads were taped in place, and the end of a syringe was cut off and positioned over the new nipple to protect it and then taped into place with the loose sterile pads. This type of construction wherein much manipulation of the bandage was necessary has proven to not be as sterile as desired. Also the manipulation has not been comfortable to the patient, and the patient could not herself as a practical matter make and change her own bandage. It also often would not be form fitting so as to minimize discomfort resulting from excess contact with the newly formed tissue. Often the bandage would not sufficiently protect the new tissue from the unsanitary environment especially if not carefully applied. Further, the involved manipulating procedure of constructing and applying this bandage and its "jury-rigged" appearance can be discomforting to women who have undergone the emotional trauma of a radical mastectomy.

Accordingly, it is the principle object of the present invention to provide a new improved bandage for the nipple and areola area of a breast which has undergone a radical mastectomy.

Another object of the present invention is to provide a novel wound protector for the areola and nipple area which protector is ready for use and can be quickly and easily applied by the woman who has undergone a radical mastectomy.

A further object of the present invention is to provide an improved bandage for the areola and nipple which is carefully configured so as to minimize contact with the reconstructed tissue and to minimize any resulting discomfort.

A still further objest is to provide a novel bandage designed for the areola and nipple area which provides aeration of the nipple to promote healing while minimizing communication with the unsanitary environment.

Another object is to provide an improved surgical wound protector bandage construction which has the appearance of professional and sound manufacture so the patient will be more confident and at ease with it.

Other objects and advantages of the present invention will become more apparent to those persons having ordinary skill in the art to which the present invention pertains from the following description taken in conjunction with the accompanying drawings.

BRIEF DESCRIPTION OF THE DRAWINGS

FIG. 1 is a perspective view of a surgical wound protector of the present invention showing it being applied to the breast of a woman who has undergone a radical mastectomy.

FIG. 2 is a top plan view of the wound protector of FIG. 1.

FIG. 3 is a side elevational view of the wound protector of FIG. 1 before application.

FIG. 4 is a side elevational view of the nipple protector member of the surgical wound protector of FIG. 1 shown in isolation.

FIG. 5 is a top plan view of the nipple protector member of FIG. 4.

FIG. 6 is a side elevational view showing in schematic form the securing of the protector member of FIG. 4 to the underlying pad.

DETAILED DESCRIPTION OF THE PREFERRED EMBODIMENT

Referring to FIG. 1 a surgical wound protector of the present invention is illustrated generally at 10 and is formed of three basic components: a generally circular sterile pad 12, a nipple protector member centrally positioned on the pad and shown generally at 14, and a tape securing construction 16 designed to both hold protector member 14 to sterile pad 12 and also to hold the sterile pad and protector member to the woman's breast 17 when positioned over the nipple 18 and areola 19.

Pad 12 is a sterile pad of about 3/16 inch thickness and having a 2½ inch diameter as shown at 20. It has a nonsticking lower surface 21 to be positioned against the patient's breast 17, an upper surface 22, and a ¾ inch diameter hole 24 centrally positioned and passing through the pad.

Protector member 14 is cone-shaped and has a dome-shaped top 26 and a base portion 28. An annular flange 29 extends radially out from base portion 28 and has an outer diameter of 1.25 inches as shown at 30 in FIG. 5. The diameter of base portion 28 is 1.00 inches as depicted in the drawings by numeral 31. At the tip of dome-shaped top 26 are four symmetrically spaced holes 32 each having a diameter of about 0.062 inches and providing aeration of the enclosed nipple 18 while protecting it from the unsanitary environment. Nipple protector member 14 is formed of a tissue-compatible plastic material; the plastic material is preferably clear so that the healing condition of the nipple 18 can be easily be viewed without removing wound protector 10. Protector member has a height of 0.88 inches as shown at 34 in FIG. 4 and a diameter of the dome-shaped top as best shown in FIG. 4 at 36 of 0.62 inches. As can be appreciated, the interior of nipple protector member 14 is configured to receive the nipple 18 therein but is slightly larger so as to minimize the contact with the nipple once in position. Centrally located hole 24 in the pad is slightly smaller than the base portion hole 37 in the protector member and preferably is 0.750 inches in diameter. Thus, as can be appreciated from FIG. 6, the delicate nipple tissue will touch the softer pad 12 which will soften any impact with the harder plastic nipple protector member 14.

Tape securing construction 16 is provided for both securing the nipple protector member 14 to pad 12 as well as for securing pad 12 and protector member 14 over the nipple 18 and to the patient's breast. It comprises a continuous piece of tape having an inner circular portion 38 and four perforated tape strips 40 extending radially out from the circular portion. Inner circular portion 38 has a 0.875 inch diameter hole 42 in the center which then fits over protector member 14 as best illustrated in FIG. 6 engaging the upper surface of annular flange 29 to thereby hold the nipple protector member 14 securely on upper surface 21 of the pad. The inner circular portion 38 of the tape is slightly smaller than pad as best shown in FIG. 2, thereby defining a rim 43 of gauze pad so that the edges of circular portion 38 do not rub against the breast. Tape securing construction 16 is formed of a breathable FDA approved pressure sensitive tape, preferably perforated, and a protective paper tape 44 as shown in FIG. 3 removable before application is provided on the back surface of each one of the tape strips 40. As best illustrated in FIG. 2, tape strips 40 are positioned ninety degrees relative to each other and are 1.00 inch long typically as shown at 46 and 0.75 inches wide typically as shown at 48 and thus will extend 4.50 inches typically from the tip of or outer end of one strip to the outer end of the opposite diametrical strip as depicted by dimension 50.

The surgical wound protector 10 of the present invention then will be individually packaged in a sterile package which can easily be torn open by the user. As can be appreciated, the subject surgical wound protector is convenient to apply to the breast by the doctor or other medical personnel as well as by the patient herself. It is constructed so as to minimize contact with the delicate nipple and areola area and also constructed so as to promote healing of this area. Further, the subject surgical wound protector presents a professionally sound appearance so as to give the patient more confidence in its use.

From the foregoing detailed description, it will be evident that there are a number of changes, adaptations, and modifications of the present invention, including changes to the various dimensions and materials stated herein, which come within the province of those skilled in the art. However, it is intended that all such variations not departing from the spirit of the invention be considered as within the scope thereof as limited solely by the claims appended hereto.

What is claimed is:

1. An areola/nipple surgical wound protector comprising:
   a sterile pad having an upper surface, a lower surface, and a centrally-located opening therethrough engaging said upper and lower surfaces,
   a cone-shaped nipple protector formed of tissue-compatible transparent plastic, and having a base portion and a top portion,
   said nipple protector member having at said base portion a radially-disposed flange with an upper annular flange surface,
   a securing means for securing said base portion to said sterile pad upper surface and over said centrally-located opening, and for securing said sterile pad to the patient's breast so that the patient's nipple passes up through said opening and into said nipple protector member,
      said securing means directly securing said flange to said upper surface of said pad,
      said securing means including a continuous tape member engaging said upper annular flange surface and a plurality of tape strips radially disposed out from said pad, and
   said top portion defining at least one air hole passing therethrough for aerating the patient's nipple positioned in said nipple protector member.

2. The protector of claim 1 wherein said air hole has a diameter of 0.062 inches.

3. The protector of claim 1 wherein said at least one air hole comprises four spaced air holes.

4. The protector of claim 3 wherein each said air hole has a diameter of about 0.062 inches.

5. The protector of claim 1 wherein said flange has a width of 0.125 inches.

6. The protector of claim 1 wherein said top portion is smooth and rounded and forms a downwardly-disposed dome.

7. The protector of claim 1 wherein said plurality of tape strips comprises four tape strips spaced ninety degrees relative to each other.

8. The protector of claim 1 wherein said continuous tape member comprises an inner circular tape portion having a central opening through which said nipple protector member passes and said tape strips extending radially out from said inner circular tape portion.

9. The protector of claim 8 wherein the diameter of said inner circular tape portion is less than that of said pad.

10. The protector of claim 1 further comprising removable protective paper tape on the inner surface of said tape strips.

11. The protector of claim 1 further comprising a sterile package enclosing said sterile pad, said nipple protector member, and said securing means.

12. The protector of claim 1 wherein said sterile pad comprises a circular 2½ inch diameter non-sticking 3/16 inch thick sterile pad and said centrally-located opening has a ¾ inch diameter.

13. The protector of claim 1 wherein said nipple protector member has a one inch diameter at said base portion and a height of ¾ inch.

* * * * *